United States Patent [19]
Shapira et al.

[11] Patent Number: 5,192,267
[45] Date of Patent: Mar. 9, 1993

[54] VORTEX SMOKE REMOVER FOR ELECTROSURGICAL DEVICES

[76] Inventors: Nadiv Shapira, 5249 LaJolla Hermosa Ave., LaJolla, Calif. 92037; John T. M. Wright, 10831 Oehlmann Ave., Conifer, Colo. 80433

[21] Appl. No.: 678,169

[22] Filed: Mar. 28, 1991

Related U.S. Application Data

[63] Continuation of Ser. No. 300,180, Jan. 23, 1989, abandoned.

[51] Int. Cl.⁵ ............................................. A61B 17/20
[52] U.S. Cl. ........................................ 604/22; 604/35; 606/28; 606/45
[58] Field of Search .................. 406/152; 55/456, 457; 15/415.1; 366/339; 128/395, 399, 783, 800; 606/2-13, 27-40; 604/19, 20, 22, 73, 93, 118, 317, 35, 902, 903, 119; 137/808-812; 138/37, 42, 39

[56] References Cited

U.S. PATENT DOCUMENTS

| | | |
|---|---|---|
| 818,891 | 4/1906 | Jones et al. |
| 1,086,763 | 2/1914 | Goersch .............................. 55/456 |
| 1,411,606 | 4/1922 | Brereton ............................. 55/457 |
| 2,020,194 | 11/1935 | Kuhlman ............................ 138/37 |
| 2,068,496 | 1/1937 | Linghammar .................. 15/415.1 |
| 2,275,167 | 3/1942 | Bierman . |
| 2,808,833 | 10/1957 | August . |
| 2,888,928 | 6/1959 | Seiger . |
| 3,182,675 | 5/1965 | Zilberfarb et al. ............... 137/808 |
| 3,266,492 | 8/1966 | Steinberg . |
| 3,394,533 | 7/1968 | Yi Sheng Li et al. . |
| 3,495,385 | 2/1970 | Glass . |
| 3,508,561 | 4/1970 | Cornish, III ...................... 137/808 |
| 3,828,780 | 8/1974 | Morrison, Jr. . |
| 3,902,494 | 9/1975 | Haberlen et al. ................... 604/20 |
| 3,906,955 | 9/1975 | Roberts . |
| 3,947,939 | 4/1976 | Steiner ................................ 138/39 |
| 3,964,484 | 6/1976 | Reynolds et al. ................. 604/902 |
| 3,974,833 | 8/1976 | Durden, III . |
| 3,982,541 | 9/1976 | L'Esperance, Jr. . |
| 4,002,170 | 1/1977 | Hansen et al. .................... 604/902 |
| 4,022,218 | 5/1977 | Riddick .............................. 604/902 |
| 4,074,718 | 2/1978 | Morrison, Jr. . |
| 4,112,950 | 9/1978 | Pike . |
| 4,170,234 | 10/1979 | Graham . |
| 4,197,869 | 4/1980 | Moncrief-Yeotes ............... 137/808 |
| 4,275,731 | 6/1981 | Nichols ............................. 604/319 |
| 4,362,160 | 12/1982 | Hiltebrandt . |
| 4,466,741 | 8/1984 | Kojima ............................... 138/37 |
| 4,562,838 | 1/1986 | Walker . |
| 4,683,884 | 8/1987 | Hatfield et al. . |
| 4,686,981 | 8/1987 | Forintos . |
| 4,688,569 | 8/1987 | Rabinowitz . |
| 4,719,914 | 1/1988 | Johnson . |
| 4,747,405 | 5/1988 | Leckrone ............................ 606/16 |

FOREIGN PATENT DOCUMENTS

2118295  10/1983  United Kingdom ............... 137/808

*Primary Examiner*—John D. Yasko
*Assistant Examiner*—Anthony Gutowski
*Attorney, Agent, or Firm*—Browdy and Neimark

[57] ABSTRACT

A smoke removing device used with an electrosurgical device consists of a a hollow tube for evacuating the smoke, a tubular housing including vortex means for creating a vortex at an entrance end of the tubular housing, and an exit end of the tubular housing connected to one end of the hollow tube, another end of the hollow tube being connected to a suction means for creating suction to remove the smoke from the air near the electrosurgical device.

17 Claims, 5 Drawing Sheets

VORTEX SMOKE REMOVER FOR ELECTROSURGICAL DEVICES

This application is a continuation of application Ser. No. 07/300,180, filed Jan. 23, 1989, now abandoned.

FIELD OF THE INVENTION

The present invention relates to improvements in smoke removal and, more particularly, to smoke generating devices such as an surgical electrocautery device having a vortex creating vacuum smoke remover.

BACKGROUND OF THE INVENTION

The use of hand-held electrosurgical instruments such as electrocautery or laser surgical devices is used in many branches of surgery for the bloodless cutting of tissue, and for the cauterizing of vessels to stop bleeding. During surgical use the localized heat generated by the electrical discharge cause large amounts of noxious smoke to be produced. This high temperature smoke rises rapidly from the point of the cautery instrument. Various studies have indicated that the smoke may contain carcinogenic elements, potentially harmful to the operating room staff. In addition the smoke is sometimes produced in such volume that the surgeon's view of the operative field is obscured. In other circumstances, the anatomy causes the smoke to be trapped. Such a case is the dissection of the left internal mammary artery for subsequent coronary artery bypass grafting. The internal mammary artery lies beneath the left rib cage, several centimeters to the left of the midline incision. The smoke generated during the dissection of the vessel tends to collect in the chest cavity. It is therefore desirable to provide a smoke collection system to remove the nuisance, smell and potential hazard of the smoke. At the same time, the collection system should not unduly interfere with the surgeon's field of view of the tissues being cut, nor can the device interfere with the use of the electrosurgical instrument.

A number of electrosurgical devices are available which do not include any suction capabilities for removing smoke from the operating area. For example, U.S. Pat. Nos. 4,074,718, 4,112,950, 4,170,234, and 4,688,569. Additionally, other U.S. patents disclose devices which do include suction capabilities. For example, U.S. Pat. Nos. 2,275,167, 3,266,492, and 3,906,955 disclose such devices. These devices include a tube connected to a source of vacuum which runs parallel to the cautery blade. U.S. Pat. No. 4,362,160 discloses an endoscope which includes passages for feeding in and drawing off scavenging or flushing liquid which extend longitudinally behind the cutting or coagulating loop.

It is further known to attach suction means to electrocoagulating devices, as shown in U.S. Pat. Nos. 2,808,833, 2,888,928, and 4,686,981. However, U.S. Pat. Nos. 2,808,833 and 4,686,981 include suction means for the express purpose of withdrawing excess blood prior to coagulating the remaining blood. U.S. Pat. No. 2,888,928 discloses a coagulating surgical instrument which includes a plurality of openings disposed at right angles with respect to the longitudinal axis of the cautery tip. Therefore, the suction operates to clear an area which is not immediately adjacent to the coagulating instrument. Other patents, such as U.S. Pat. Nos. 3,974,833, 4,562,838, 4,683,884, and 4,719,914 disclose an electrosurgical instrument with a smoke dissipating means which is concentric with the cutting blade, or in the case of U.S. Pat. No. 3,982,541 concentric with the laser beam passage.

The processes using electrosurgical devices such as cauterization, laser surgery, and coagulation, are very different procedures. Cauterization involves the use of a hot iron, an electric current or a caustic substance to destroy to tissue. Laser surgery involves the use of a precisely controlled laser beam to cut or destroy tissue. Coagulation deals with the process of blood clot formation.

Although the various patents dealing with these devices disclose the general principle of providing a suction passage to the cutting or business end of the device, their particular constructions create difficulties in their use. Namely, they are limited by their structure to removing smoke which is close to the inlet of the suction means. In particular, the structures are such that the vacuum input tube remains very close to the tip of the electrocautery blade generating the smoke. Thus, the surgical field may be obscured from view either by smoke, or by the vacuum input tube itself. In those patents in which the vacuum input tube is far from the cutting surface, the suction is likely to be ineffective in removing all smoke from the surgical field because of the distance between the vacuum input tube and the cutting surface.

Further, in a number of these prior art devices, it is not possible to effectively remove the smoke because the suction tube or passage becomes clogged with blood. It is of the utmost importance that smoke created by the electrocautery, laser surgical or coagulation device be efficiently removed from the surgical field. Smoke created by these devices is suspected of being carcinogenic and mutagenic. Thus, it is necessary to remove the smoke from the surgical field to insure the surgeon's safety.

The smoke created by these devices must also be efficiently removed from the surgical field because it obscures the surgeon's view of the surgical field and is an irritant to the surgeon's eyes. The smoke is odorous and interferes with the surgeon's concentration during the operation.

U.S. Pat. Nos. 818,891, 3,394,533 and 3,495,385 disclose devices which include helical shaped members through which fluids flow, although none of there patents discuss the use of a helical element for smoke removal.

SUMMARY OF THE INVENTION

The present invention improves smoke removability by providing a vortex creating portion in the form of a helical member at the intake of the smoke removing tube. Webster's New Collegiate Dictionary defines a vortex as "a mass of fluid having a whirling or circular motion tending to form a cavity or vacuum in the center of the circle, and to draw toward this cavity or vacuum bodies subject to its action." In the present invention, the creation of the vortex suction causes smoke to be pulled in from a wider area, from a greater distance, and at a quicker rate than that available using an unaltered smoke removing tube.

It is therefore one of the object of the present invention to provide an improved smoke removal device which can be used during electrosurgery to remove smoke created during an operation.

It is a further object of this invention to provide an improved smoke removal device which is in combination with an electrosurgical device.

It is a further object of this invention to provide an improved smoke removal device which efficiently removes smoke from the surgical field.

It is a further object of this invention to provide a smoke removing device which insures the surgeon's safety.

It is a further object of this invention to provide a smoke removing device which efficiently removes smoke from the surgical field so that the surgeon's concentration is not interfered with during the surgical procedure.

It is a further object of this invention to provide a smoke removing device which uses a vortex in a tube to create a whirlpool motion outside the tube resulting in increased amounts of smoke being sucked into the tube.

It is a further object of this invention to provide a smoke removing device by which smoke is removed more effectively then the prior art devices when the tube inlet is farther away from the cutting surface.

It is a further object of this invention to use the smoke removal device of the present invention to remove smoke, or other noxious atmospheres, as required in other fields including, but not limited to, smoke removal necessary for restaurants, fire fighting, and various other industrial applications.

According to the present invention, a device for removing smoke from the air near a smoke generator is provided comprising a hollow tube for evacuating the smoke, a tubular housing including vortex means for creating a vortex at an entrance end of the tubular housing, and an exit end of the tubular housing adapted to be connected to one end of the hollow tube, another end of the hollow tube being adapted to be connected to a suction means for creating suction to remove the smoke from the air near the smoke generator.

The smoke generator may be an electrosurgical device.

An electrosurgical device is provided which includes a cutting and cauterizing means in electrical communication with an external power source, a tube having a vortex end and adapted to be connected to a vacuum generator for removing smoke created with the cutting and cauterizing means from an adjacent immediate area, and means for turning on and off the vacuum suction device located at a distance spaced from the cutting and cauterizing end of the device.

Still other objects, features and attendant advantages of the present invention will become apparent to those skilled in the art from a reading of the following detailed description of the embodiments constructed in accordance therewith, taken in conjunction with the accompanying drawings

BRIEF DESCRIPTION OF THE DRAWINGS

These and other objects of the present invention will become clearer when considered with the drawings and the detailed description of the preferred embodiments, shown by way of example in the drawings in which.

DETAILED DESCRIPTION OF THE PREFERRED EMBODIMENTS

Figures 1, 1A, 2, 3, 4A, 4B, 4C, 5:
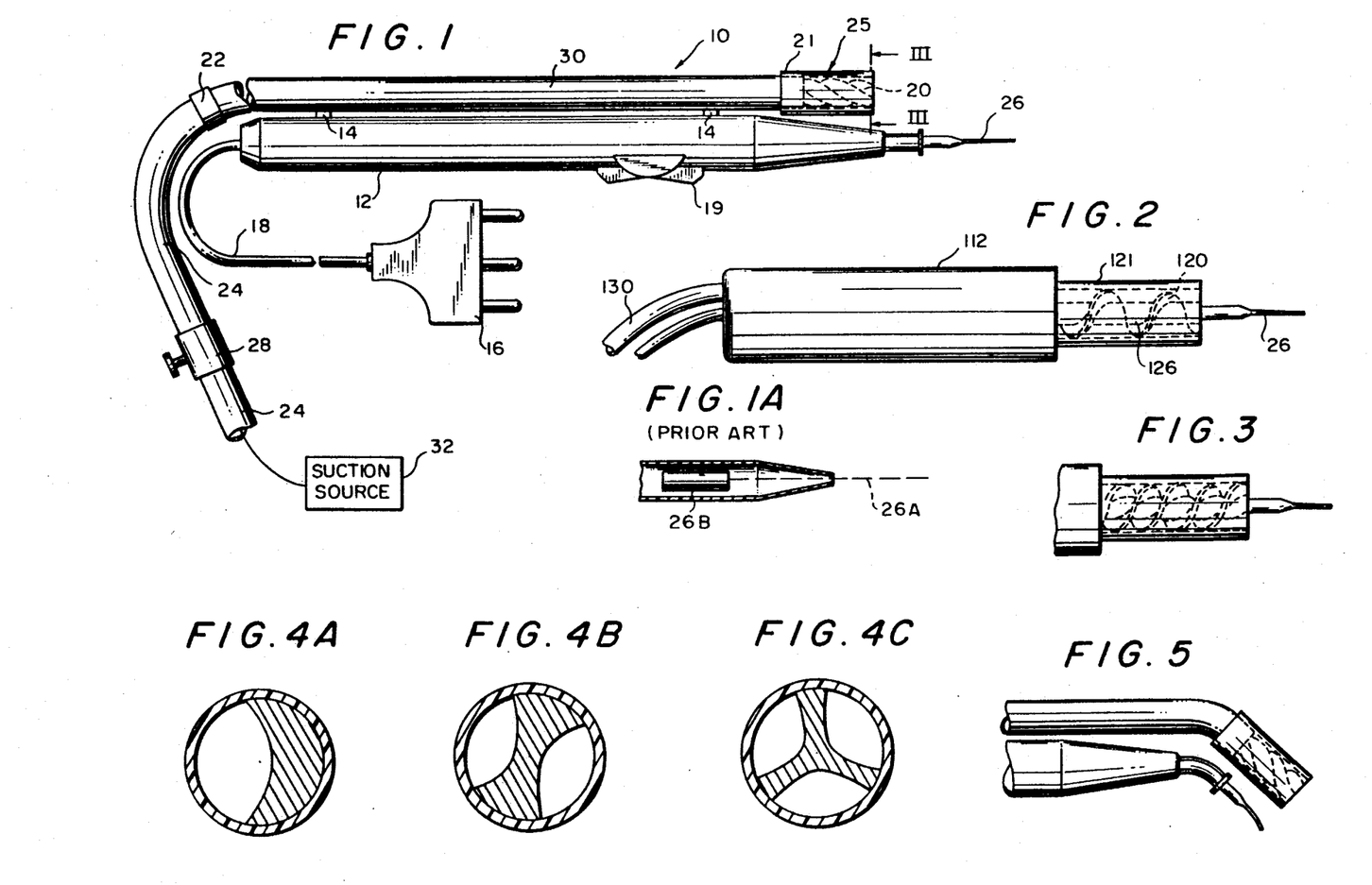
FIG. 1 is a plan view of an electrosurgical device including the smoke removal device according to a first embodiment of the present invention.
FIG. 1A is a plan view of a prior art electrosurgical laser tipped cutting instrument as discussed in the "BACKGROUND OF THE INVENTION" section above.
FIG. 2 is a plan view of an electrosurgical device including the smoke removal device according to a second embodiment of the present invention.
FIG. 3 is a plan view of a third embodiment of the present invention.
FIGS. 4A, 4B, and 4C are a set of cross-sectional views of different vortex creating tubes which can be used in accordance with the present invention, taken along the line III—III of FIG. 1.
FIG. 5 is a plan view of a fourth embodiment of the present invention in which the tip of the electrocautery device and the vortex tip of the suction tube are roundly curved.

FIG. 1 schematically shows a typical electrosurgical cutting or coagulating device 12. One embodiment of the present invention is one in which the smoke remover device 10 is removably attached to device 12. The remover 10 can be attached to the electrosurgical device using various types of attaching means 14 such as mounting brackets or the like. The electrosurgical device 12 receives power from a power source (not shown) through plug 16, which can be adapted to fit various power sources, and then through electrical cord 18 to the device 12.

The smoke remover 10 consists of a hollow tubular base 30 and a vortex creating member 25 attached to the base 30. Tube 21 and base 30 may be constructed of plastic. The vortex creating member 25 includes a twisted piece of material 20, for example, stainless steel fit within a tube 21. As an example, a section of drill bit wedged within an appropriately sized tube will provide the desired effect. The vortex creating member 25 is removably inserted onto the end of base 30.

A set of interchangeable tips including the straight vortex tip shown in the present embodiment in FIG. 1 may be provided. The various tips are interchangeable as the situation requires to enable the operating surgeon to clear away the maximum amount of smoke. Some of the various tips that could be used include the straight vortex tip 20 of the embodiment shown in FIG. 1, a sharply or roundly curved vortex tip such as shown in FIG. 5, and various other tips. Additionally, various tips may be provided in which the twisted material 20 is of different lengths.

The smoke remover 10 is attached at attaching joint 22 to a vacuum hose 24 which is attached to a suction source 32 shown schematically on FIG. 1 at the opposite end of hose 24.

FIG. 1A shows a prior art laser tipped cutting instrument as an example of the laser type hand-held prior art electrosurgical instruments listed in the "BACKGROUND OF THE INVENTION" section above.

This prior art device is shown having a laser beam 26A and a laser source 26B which function to permit bloodless cutting of tissues in an equivalent manner to prior art electrocautery devices also listed with such prior art hand-held electrosurgical instruments.

An alternative embodiment of the present invention is shown in FIGS. 2 and 3. In these embodiments the vortex tip 120 concentrically surrounds the base 126 of the cutting blade 26. The vortex tip 120 can be either removably or permanently attached to the electrosurgical device 112. If the tip 120 is removable then it may be part of a set of interchangeable tips which can be used as the situation requires. A tube 130 is shown coming out of the back of the electrosurgical device 112 to carry the removed smoke to hose 24, which meets tube 130 at intersection joint 22 (not shown). Of course, the tube 130 could be eliminated with the hose 24 directly to the smoke removal device 120 or the back of the electrosurgical device 112.

FIG. 4 shows cut-away cross-sections of three different vortex creating members, along the line III—III of FIG. 1, which could be used in the present invention. The member may be formed in a variety of different shapes, length, and sizes. For example, the piece 20 within the tip may be one-quarter, one-half or one inch long. Additionally, a different number of vanes may be provided in different tips. The member may be either a single or a double helix. For example, FIG. 4A has a single vortex creating opening and would be relatively easy and inexpensive to manufacture. FIGS. 4B and 4C includes two and three vanes, for creating two and three vortex creating openings, respectively and are more complicated and would thus be more expensive to manufacture. FIGS. 2 and 3 illustrate different helical configurations for the vortex member. Other variations of vortex creating members can be easily created and all are intended to be included in the present invention.

The smoke remover 10 system works in the following manner. As the heated cutting blade or electrode 26 of the electrosurgical device 12 makes contact with the patient, smoke is produced from the burning tissue. When the vortex tip 20 is attached to the smoke remover 10, the pressure differential created by the vortex causes increased circulation of the air and smoke just outside of the vortex. Because of the funnel or whirl pool effect created by the pressure differential, smoke can be sucked to the openings form between the vortex creating member and the inside of the tube in from a wider area, from a greater distance, and at a quicker rate.

In fact, the suction of the device 10 is continuous. The suction can be applied even when the blade 26 is not cauterizing. Therefore a negative pressure exists around the blade prior to generation of any smoke and the smoke is never given an opportunity to accumulate at the point of surgery.

Depending on the circumstances of the surgery involved, different vortex tips could be selected to maximize the benefits available using the vortex tip according to the present invention. In situations where the smoke is dissipating over a wider area, the straight vortex tip may provide the most benefit. However, in situations where the smoke is dissipating very slowly over a small area, a venturi vortex tip having a tapered end may be the most efficient choice. In situations where the cutting tip 26 is bent at an angle, the most efficient smoke removing tip might be the bent vortex tip. Additionally, the surgeon could also change the tips for obtaining a vortex having a different strength depending on the length of the helical member. Since the surgeon ca easily change tips on the smoke remover, the surgeon will quickly become familiar with which tip is most effective for each situation incurred.

The on-off switch for the electrocautery device is shown at 19 in FIG. 1. This is separate from the on-off for the suction.

The suction for the smoke remover 10 can be turned on using various types of valves such as valve 28 on the hose 24. The valve 28 is preferably placed on the hose 24 a few feet away from the smoke remover 10 so that the physician can ask a nurse or another member of the support staff to turn the suction on and off, thus keeping his free hand available for other purposes. The valve 28 could just as easily be placed on the smoke remover itself near the cutting edge although it is less desirable for the aforementioned reason. The presence of the valve allows the surgeon to request that the suction be turned off when it is not required in order to eliminate the noise created by the suction source.

The system according to the embodiments shown in FIGS. 2 and 3 is operated in the same manner as the first embodiment with the only difference being that smoke can be removed immediately after it forms since the smoke remover 120 is so close to the source of the smoke.

A number of tests were carried out in order to determine the efficacy of different devices to clear smoke from an operating area.

TEST 1

In a first experiment, smoke was generated using a regular Bovie machine, coagulation set at 100. In the first test, smoke was generated from a blood clot, in the second test, from a small piece of adipose tissue. In both cases the tissue was placed on a regular grounding pad. While smoke was generated, a regular operating room suction device was held with the other hand, and its position was changed in relation to the electrocautery tip (i.e above or below the tip). In addition, the suction was moved closer and away from the source of the smoke. Five different tips were attached to the suction:

1) A regular ¼" tube.
2) A narrowed tip.
3) A ¼" tube into which a piece of approximately ¼" long of a ¼" drill bit was snugly inserted.
4) Similar to #3, but with a 1" piece of drill bit.
5) A mold made of acrylic on a ¼" drill, 1 and ¼" long.

The second tip was designed to create a bernouli effect. The last three tips were designed to generate a vortex suction.

Although a precise quantitative measurement of the smoke clearance could not be done, an assessment of the clearance and the relative effectiveness of each tip could be accomplished. Testing of each tip was repeated about 10 times and the impressions were consistent. The most effective clearance was accomplished with tip #4, tips #3 and #5 were about the same, and tips #1 and #2 were the least effective. The effectiveness was manifested by the wider area of smoke clearing and by the degree of completeness of clearing. Positioning of the suction tip below the pencil did not detract significantly from its function. At times, two streams of smoke could be seen entering the suction tip.

TEST 2

A second experiment was carried out in order to substantiate the previous observation that the #4 vortex tip was superior to the other tips. This tip (¼" tubing into which a 1" long portion of a ¼" drill bit was inserted), was compared to a regular ¼" tubing. In this experiment, a piece of beef fat was used, 5×5×10 cm, utilizing again a regular bovie and suction system. Two method for assessment of the efficacy of smoke clearance were used, each repeated 10 times.

The first experiment was done while the bovie pencil was held straight up, and the suction tip perpendicular to the pencil, 1.5" above the pencil tip. In this position, the generated smoke climbed as a column along the pencil. When the suction tip was held very close to the pencil, there was a very efficient smoke clearance. As a matter of fact, the smoke could be clearly seen to divert abruptly from the pencil in a right angle towards, and opposite from, the suction tip. As the suction tip was slowly moved away from the pencil, the column of smoke initially continued to be cleared in a similar fashion, until a certain distance, in which part of the smoke was not cleared any more and rose upwardly. This distance was always longer when the vortex tip was employed, by approximately 30 to 40%, when compared to the clearance distance of the non-vortex tip. The distance was dependent on the amount of smoke generated. When high quantities of smoke were generated, the suction tip had to be held relatively closer in order to achieve a complete clearance, and visa versa. Yet, for any amount of smoke, the vortex tip was able to clear the smoke from a longer distance.

In the second set of experiments, the diameter of the area from which the smoke was cleared was assessed. When the bovie pencil tip was brought from the side rather than from above, the smoke was generated in all directions, and was spreading like a ball. At times, smoke was even coming out from areas not in direct contact with the bovie tip. Comparison of the suction tips was performed by moving them towards and away from the bovie tip where the smoke was generated. When the non-vortex suction tip was used, the smoke "ball" was very large, and the suction tip had be held fairly close to the bovie tip in order to clear all the smoke. In contrast, the vortex tip could be held at a distance approximately twice as long, and still cleared the smoke very effectively. The smoke could be seen spreading like a ball, at times 5-7 cm in diameter, and converge back towards the suction tip.

From these experiments, it can be seen that the vortex suction effects the air surrounding the tip in both distance and diameter. Thus vortex suction is capable of creating a more effective suction by the same vacuum source.

TEST 3

A third test was conducted to further demonstrate the efficiency of the vortex tube.

The objective of this experiment was to determine the smoke removal efficiency for the following tip configurations:

(a) determine the efficiency, with and without a vortex inducer in the tip; and (b) vary the diameter of the proposed vacuum cautery orifice.

In summary, it was demonstrated that an orifice with a increased diameter and a vortex inducing insert showed significantly greater smoke removal. Using a vortex enabled placement of the orifice approximately 50% further away from the smoke source as compared to an orifice without the vortex and without reducing the efficiency of smoke removal.

Figure 6:
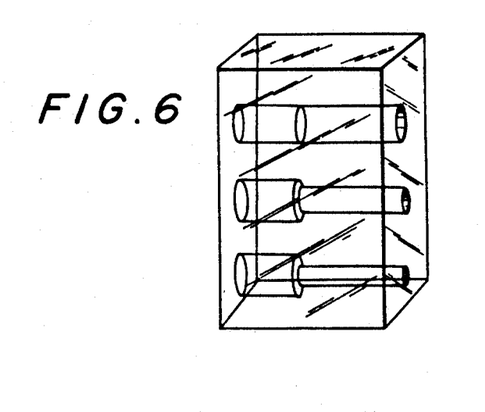
FIG. 6 is a block diagram of three orifice diameters used to demonstrate the efficiency of the vortex tube according to the present invention.

In order to carry out the experiment, three orifice diameters were machined into a block of clear acrylic to a depth of 25.4 mm (1.0 inches—see FIG. 6). The diameters were 6.35 mm (¼"), 4.76 mm (3/16"), and 2.38 mm (3/32"). The corresponding drill bit sizes were cut to a length of 25 mm and inserted into the block when measurements were needed "with vortex". The drills acted to induce spiral air flow. A ¼" I.D. hole on the distal side of the acrylic block served to connect the vacuum source with the test orifice. The sides of the orifice tips were at sharp right angles. It was estimated that the drills blocked approximately 40% of the orifice area.

The 6.35 mm (¼") maximum size orifice was chosen because it was equal to the vacuum hose I.D. used in the operating room. Any larger diameter would decrease the vacuum efficiency by dissipating the air flow lines from the orifice.

Figure 7A:
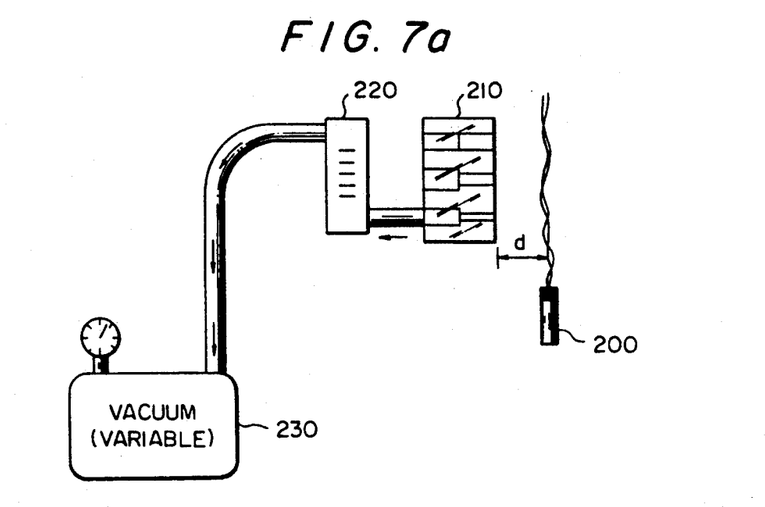
FIG. 7A illustrates the circuit used to measure the efficiency of the vortex tube.

The circuit was set up per FIG. 7a. A vacuum was drawn through 6.35 mm (¼") tubing at a regulated 25 liters/minute gas flow rate. The distal end of the tubing was attached to the orifice of interest and vacuum flow initiated. Each orifice was tested without the drill first, then with the drill.

The smoke source (filtered cigarettes) was placed 6 cm inferior to the orifice and moved either towards or away from the vacuum. If no vacuum was applied, the smoke rose in a concentrated stream for approximately 10-12 cm and then progressively dissipated. Data was taken in both directions. Care was taken to avoid any interfering movement of air. A total of five samples were recorded for each parameter.

Figure 7B:
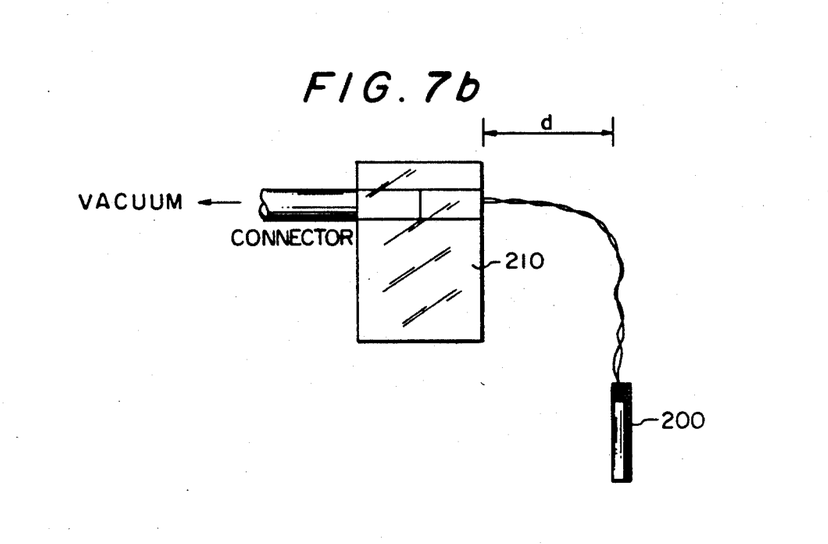
FIG. 7B illustrates the critical distance measured using the vortex tube.

The "critical distance" was defined as the distance "d" (in mm) at which the entire (100%) smoke flow curved towards the vacuum source and was drawn into the vacuum orifice at an obvious right angle to the non-vacuum rising flow (see FIG. 7b). The accuracy of the measurements was estimated to be ±2 mm. The critical distance is the measure of the smoke removal efficiency.

Figure 8:
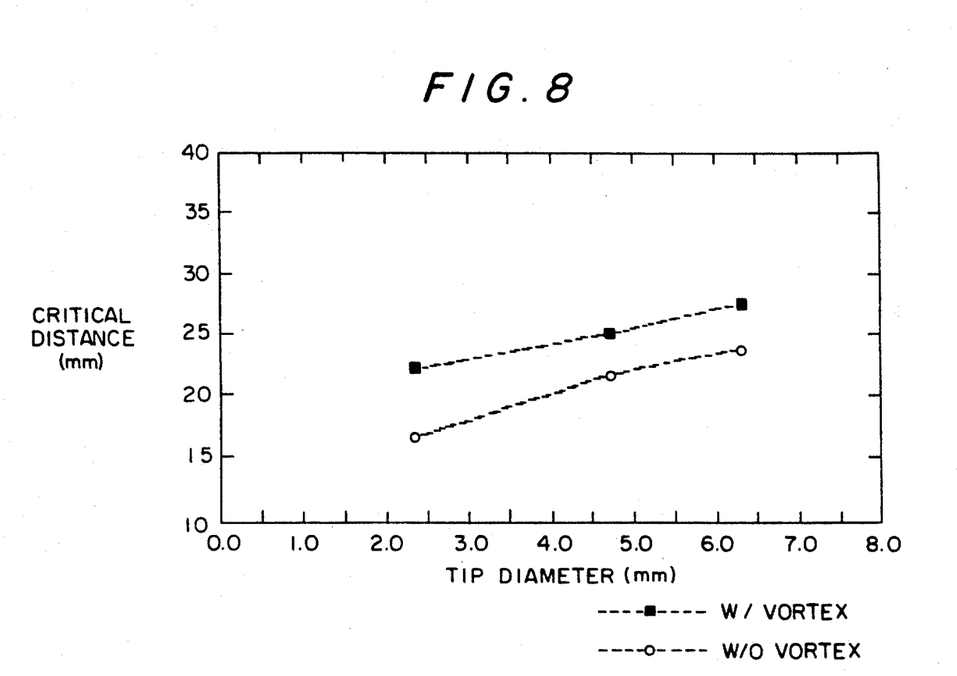
FIG. 8 is a graph of the results of the experiment conducted using the equipment of FIGS. 6 and 7.

All data is shown in Table 1 and illustrated in FIG. 8. The statistical results are in Table 2.

TABLE 1

Critical Distance Measurements with Different Orifice Sizes (distance that smoke is attracted into an orifice with a constant velocity)

| Type of Orifice | Tip Diameter (mm) | "out-to-in" critical dist. (mm) | Per-cent Improvement | "in-to-out" critical dist. (mm) | Per-cent Improvement |
|---|---|---|---|---|---|
| w/o vortex | 6.35 | 24.0 ± 0.7 | | 27.4 ± 0.5 | |
| with vortex | 6.35 | 27.6 ± 0.5 | 15.0 | 31.0 ± 1.0 | 13.1 |
| w/o vortex | 4.76 | 21.8 ± 0.5 | | 25.4 ± 0.9 | |
| with vortex | 4.76 | 25.0 ± 0.7 | 14.7 | 27.6 ± 1.1 | 8.7 |
| w/o vortex | 2.38 | 16.6 ± 0.5 | | 21.0 ± 0.7 | |
| with vortex | 2.38 | 22.2 ± 0.8 | 33.7 | 25.2 ± 0.4 | 20.0 |

Notes:
(1) The velocity (measured by a rotometer flowmeter) was 25 LPM for the orifices without drills, but dropped approximately 1 LPM (to 24) for the orifices with drills. This drop was attributed to the increase in resistance from the drill cross-section area. The flowmeter was adjusted back to 25 LPM so that the results would be comparable for both sets of data.
(2) The n = 5 for all data. All data reported as Mean ± 1 S.D.
(3) See previous discussion for the definition of "critical distance".

TABLE 2

Statistical Analysis Results (T-test)

| Data Direction | Comparison Description | | p value | Significant at 0.95? |
|---|---|---|---|---|
| out-to-in (towards the orifice) | 6.35 mm | with vortex vs without vortex | 0.0010 | Yes |
| | 4.76 mm | with vortex vs without vortex | 0.0012 | Yes |
| | 2.38 mm | with vortex vs without vortex | 0.0010 | Yes |
| in-to-out (away from the orifice) | 6.35 mm | with vortex vs without vortex | 0.0011 | Yes |
| | 4.76 mm | with vortex vs without vortex | 0.0213 | Yes |
| | 2.38 mm | with vortex vs without vortex | 0.0010 | Yes |

The efficiency of smoke removal (=increased critical distance) was greatest with the largest orifice diameter. This is consistent with flow line theory which states that the area of the orifice is proportional to the amount of air that it can "attract". It is also consistent with resistance to flow physics (the larger the orifice diameter the less the resistance to that flow).

The efficiency of smoke removal was also larger with the vortex inserts in place (see Table 2 for p values). The spirals formed seem to enhance the flow lines and increase the drawing power. There is a high probability that machining a small radius on the sharp right angles of the orifice tips would also enhance the vacuum efficiency.

There is also a possibility that the area lost to the drill cross section actually skews the results. If the orifice size was to be redefined as "effective open area" rather than orifice diameter, then it would be correct to compare, for example, data from the 6.35 mm (with vortex) to the 4.76 mm (without vortex). If this hypothesis holds true, the rationale of using a vortex would become even more apparent.

Finally, during the testing it was noticed that the closer that the orifice (vacuum source) is to the smoke source, the greater the efficiency. This was intuitively clear and was substantiated by observations.

TEST 4

A fourth set of tests were performed which used the large diameter orifice (6.35 mm) from Test 3 but varied the turn density of the insert. It concluded that a spiral density of 2 turns/25 mm has greater efficiency than a spiral density of 1 turn/25 mm.

The objective of this experiment was to determine the smoke removal efficiency for the following tip configurations:

a) Vortex that has one (1) turn in 26 mm.
b) Vortex that has one and one-half (1½) turns in 25 mm.
c) Vortex that has two (2) turns in 25 mm.

In summary, it was demonstrated that increasing the turns on the vortex inducing insert showed significantly greater smoke removal. There was an 11.2% increase in efficiency when the turn density was increased from 1 turn to 2 turns per 25 mm.

The products used in this experiment are described below.

Three vortex turn densities were constructed out of brass stock (¼" wide and 1/32" thick) to fit inside an acrylic block (machined for Test 3 described previously) to a depth of 25 mm. (per/25 mm) were one (1), one and one-half (½) and two (2). All fit inside the 0.635 mm (¼") I.D. hole on the distal side of the acrylic block. The sides of the orifice tips were at sharp right angles. It was estimated that the spirals blocked approximately 3% of the orifice area (as compared to the approximately 40% blockage for the drill inserts—see Test 3).

Figure 10A:
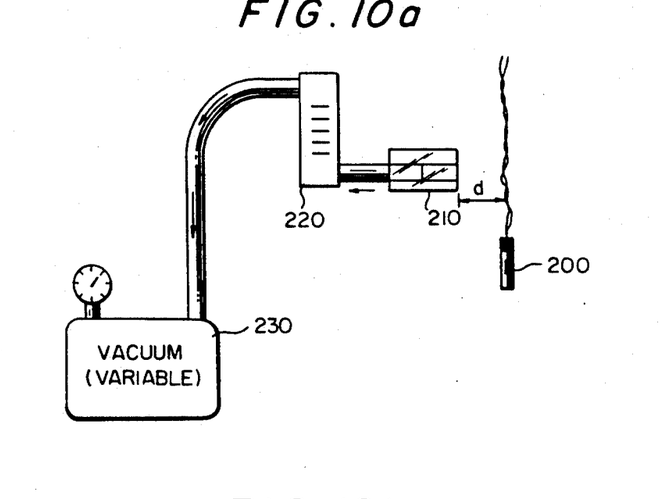
FIG. 10a shows an experiment arrangement including the location of distance "d", an orifice block and smoke source.

The circuit was set up per FIG. 10a. A vacuum was drawn through 6.35 mm (¼") tubing at a regulated 25 liters/minute gas flow rate. The distal end of the tubing was attached to the orifice and vacuum flow initiated.

The smoke source (filtered cigarettes) was placed 6 cm inferior to the orifice and moved towards the vacuum. If no vacuum was applied, the smoke rose in a concentrated stream for approximately 10-12 cm and then progressively dissipated. Care was taken to avoid any interfering movement of air. A total of five samples were recorded for each spiral.

Figure 10B:
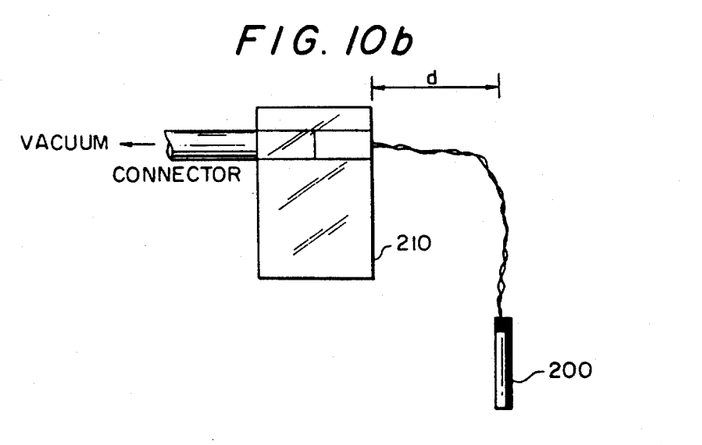
FIG. 10b is a detailed schematic view of the orifice block and smoke source with distance "d"

The "critical distance" was defined as the distance "d" (in mm) at which the entire (100%) smoke flow was drawn into the vacuum orifice at an obvious right angle to the non-vacuum rising flow (see FIG. 10b). The accuracy of the measurements was estimated to be ±2 mm.

The "starting distance" was defined as the distance "d" (in mm) at which any smoke flow was drawn into the vacuum orifice. The accuracy of these measurements was estimated to be ±3 mm.

Figure 9:
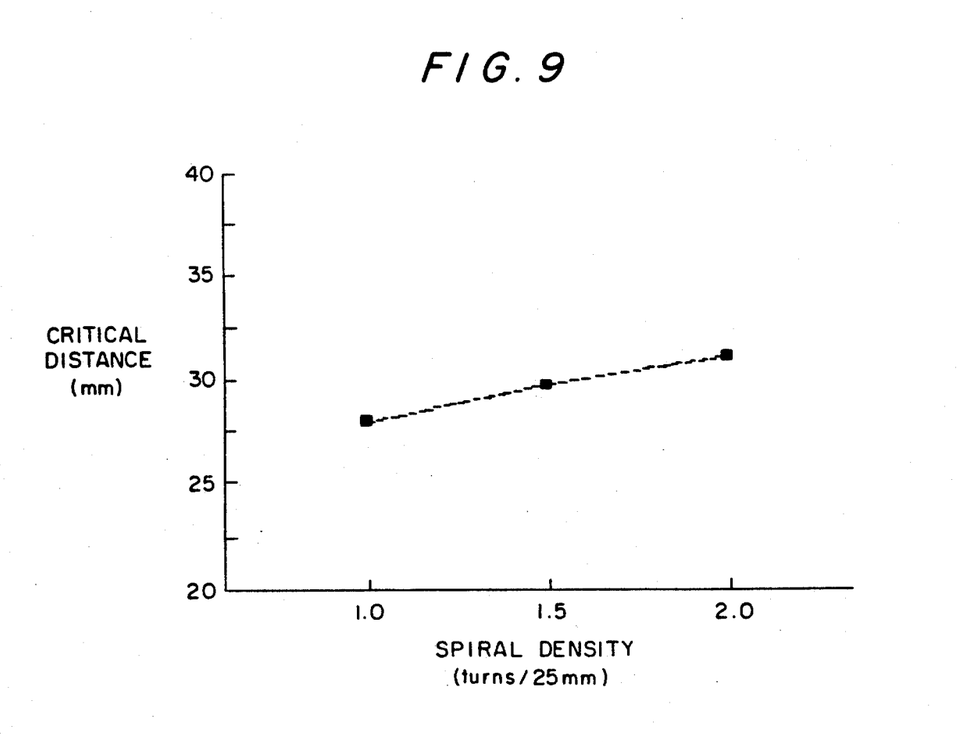
FIG. 9 shows a plot of critical distance measured against spiral density.

All data is shown in Table 3 and illustrated in FIG. 9. The statistical results are in Table 4.

The efficiency of smoke removal (=increased critical distance) was greatest with the most dense spiral (most turns/25 mm).

The critical distance was also greater for this "low cross-sectional" spiral as compared to the data obtained in Test 3 (the mean critical distance was 31.2 mm for the brass insert (2 turns) and 27.6 mm for the drill insert—a 13.0% improvement). The reproducability of this data has not been substantiated at this time, however.

The difference between the critical distance and the starting distance did not become significantly greater or smaller with an increase in turn density.

TABLE 3

Critical Distance and Starting Distance Measurements with Different Turn Densities (6.35 mm diameter)

| Turn Density (/25 mm) | Critical Distance (mm) | % Improvement over the previous spiral density | Starting Distance (mm) | % Improvement over the previous spiral density |
| --- | --- | --- | --- | --- |
| 1 turn | 28.0 ± 0.7 | | 34.0 ± 0.7 | |
| 1¼ turns | 29.8 ± 0.8 | 6.4 | 36.6 ± 0.5 | 7.6 |
| 2 turns | 31.2 ± 0.8 | 4.7 | 37.8 ± 0.8 | 3.3 |

Notes:
(1) The velocity (measured by a rotometer flowmeter) was 25 LPM. There was no detachable drop in velocity when the brass spirals were added.
(2) The n = 5 for all data. All data reported as Mean ± S.D.
(3) See previous discussion for the definition of "critical distance" and "starting distance".

TABLE 4

Statistical Analysis Results (T-test)

| Comparison Description | p value | Significant at 0.95? |
| --- | --- | --- |
| 1 turn to 1¼ turns | 0.0367 | Yes |
| 1 turn to 2 turns | 0.0054 | Yes |
| 1¼ turns to 2 turns | 0.0046 | Yes |

TEST 5

A fifth set of tests were performed which compared three orifices of constant diameter (again 6.35 mm) and constant turn density (1 turn/25 mm), but of increasing spiral length. The results show that a longer (75 mm) length yields greater efficiency than a shorter length (25 mm).

The objective of this set of tests was to determine the smoke removal efficiency for the following brass spiral tip configurations:

a) Vortex that has one (1) turn in 25 mm and is 25 mm in length.
b) Vortex that has one (1) turn in 25 mm and is 50 mm in length.
c) Vortex that has one (1) turn in 25 mm and is 75 mm in length.

In summary, increasing the length of the vortex inducing insert showed significantly greater smoke removal. There was an 26.9% increase in efficiency when the length was increased from 25 mm to 75 mm.

Figure 11:
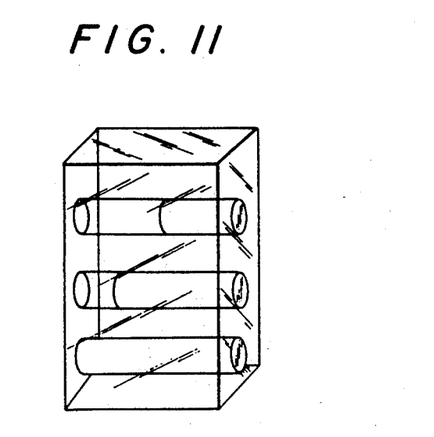
FIG. 11 is a block diagram of three orifice diameters used to demonstrate the efficiency of the vortex tube.

Three spiral lengths were constructed out of brass stock (¼" wide and 1/32" thick) to fit inside an acrylic block to a diameter of 6.35 mm (see FIG. 11). The turn density was one (1) per 25 mm. The lengths were 25, 50 and 75 mm. The sides of the orifice tips were at sharp right angles. It was estimated that the spirals blocked approximately 3% of the orifice area (as compared to the approximately 40% blockage for the drill inserts—Test 3).

Figure 12A:
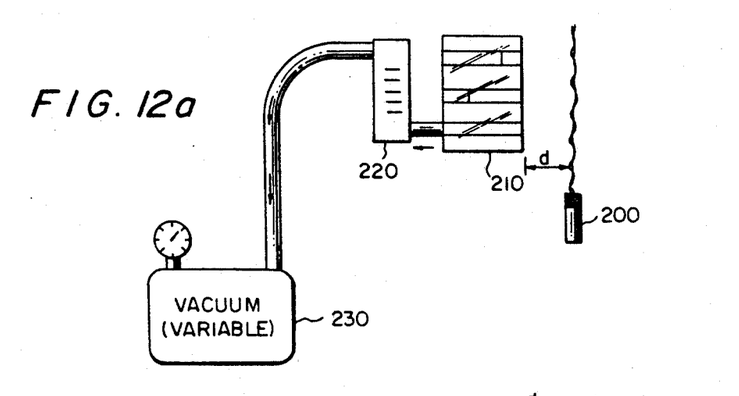
FIG. 12a is another schematic view showing a distance "d" test conducted with the three orifice block shown in FIG. 11.

The circuit was set up per FIG. 12a. A vacuum was drawn through 6.35 mm (¼.) tubing at a regulated 26 liters/minute gas flow rate. The distal end of the tubing was attached to the orifice and vacuum flow initiated.

The smoke source (filtered cigarettes) was placed 6 cm inferior to the orifice and moved towards the vacuum. If no vacuum was applied, the smoke rose in a concentrated stream for approximately 10-12 cm and then progressively dissipated. Care was taken to avoid any interfering movement of air. A total of five samples were recorded for each spiral length.

Figure 12B:
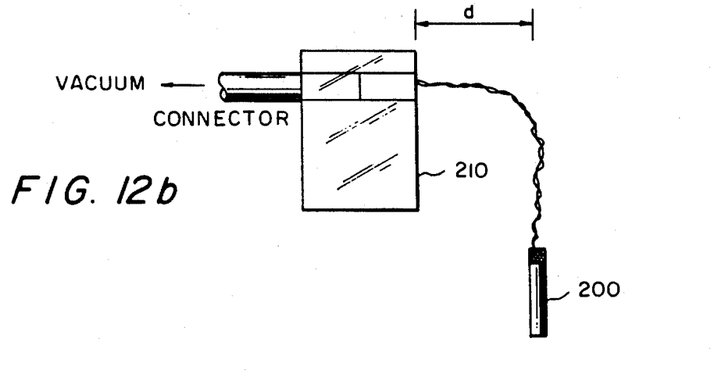
FIG. 12b is a detailed schematic view of a single orifice, distance "d" and a vacuum connection of the apparatus of FIG. 12(a).

The "critical distance" was defined as the distance "d" (in mm) at which the entire (100%) smoke flow was drawn into the vacuum orifice at an obvious right angle to the non-vacuum rising flow (see FIG. 12b). The accuracy of the measurements was estimated to be ±2 mm.

The "starting distance" was defined as the distance "d" (in mm) at which any smoke flow was drawn into the vacuum orifice. The accuracy of these measurements was estimated to be ±3 mm.

Figure 13:
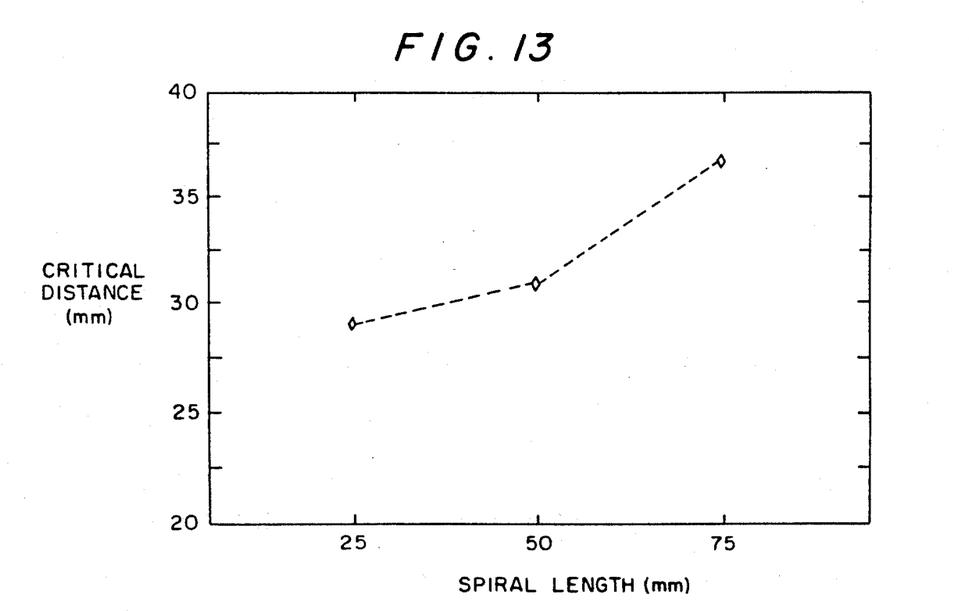
FIG. 13 is a plot of critical distance against a spiral length where the turn density is one turn per 25 millimeters.

All data is shown in Table 5 and illustrated in FIG. 13. The statistical results are in Table 6.

The efficiency of smoke removal (=increased critical distance) was greatest with the longest spiral length.

The critical distance was also greater for this "low cross-sectional" spiral as compared to the data obtained in Test 3.

The reproducability of this data seems to be quite good. If data from one (1) turn/25 mm density through a 6.35 mm diameter orifice of 25 mm spiral length is compared for the three tests done to date, results of 27.6 mm (Test 3), 28.0 mm (Test 4) and 29.0 mm (this test) are obtained.

TABLE 5

Critical Distance and Starting Distance Measurements with Increased Spiral Lengths (6.35 mm diameter)

| Spiral Length (mm) | Critical Distance (mm) | % Improvement over the previous spiral length | Starting Distance (mm) | % Improvement over the previous spiral length |
| --- | --- | --- | --- | --- |
| 25 | 29.0 ± 0.7 | | 34.4 ± 0.5 | |
| 50 | 31.0 ± 0.7 | 6.9 | 36.4 ± 0.5 | 5.8 |
| 75 | 36.8 ± 0.8 | 18.7 | 39.0 ± 0.7 | 7.1 |

Notes:
(1) The velocity (measured by a rotometer flowmeter) was 25 LPM. There was no detectable drop in velocity when the brass spirals were added.
(2) The n = 5 for all data. All data reported as Mean ± 1 S.D.
(3) See text for the definition of "critical distance" and "starting distance".

TABLE 6

Statistical Analysis Results (T-test)

| Comparison Description | p value | Significant at 0.95? |
| --- | --- | --- |
| 25 to 50 mm | 0.0217 | Yes |
| 50 to 75 mm | 0.001 | Yes |
| 25 to 75 mm | 0.001 | Yes |

The smoke removal device is discussed herein as being associated with an electrosurgical device such as a cauterizing pencil. However, it can clearly be used with any other smoke-generating surgical technique, such as coagulation or laser surgery. Moreover, it should be understood that the vortex smoke removal is adaptable for many other uses, such as smoke removal in restaurants, fire fighting and other industrial applications. For example, if a vortex creating member of the appropriate size were attached to the end of a large hose, the hose could be inserted into a burning building to remove the smoke at a faster rate, allowing fire fighters to enter the building without fear of collapsing from smoke inhalation. Additionally, if a vortex creating member were attached to a hose placed above a restaurant stove, the smoke could be cleared faster, allowing the chef to work safely and comfortably.

The foregoing description of the specific embodiments will so fully reveal the general nature of the invention that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

What is claimed is:

1. An electrosurgical device including a cutting and cauterizing means in electrical communication with an external power source, said cutting and cauterizing means engaged to a tubular housing having vortex means extending up to an end of said tubular housing for creating a vortex at an entrance end of said tubular housing, said tubular housing connected to a vacuum generator for removing smoke created with the cutting and cauterizing means from an adjacent immediate area, and means for turning on and off the vacuum created by said vacuum generator, said means for turning on and off the vacuum located at a distance spaced from an end of said cutting and cauterizing means of said device.

2. The electrosurgical device of claim 1, wherein said cutting and cauterizing means comprises an electrocautery pencil, said pencil comprising an electrode tip, wherein said tip and said tubular housing, including said vortex means, are in a roundly curved form, parallel to one another.

3. The electrosurgical device of claim 1 wherein the vortex means comprises a helical member approximately one inch long.

4. The electrosurgical device of claim 1, wherein the vortex means is a helical member forming a plurality of openings at said entrance end with an inside surface of the tubular housing through which the smoke enters at the entrance end of the tubular housing.

5. The electrosurgical device of claim 1, wherein the vortex means is a helical member extending across the inside of said tubular housing.

6. The electrosurgical device of claim 1, wherein said vortex means is a helical member extending through the center of said tubular housing.

7. The electrosurgical device of claim 1, wherein said vortex means is a helical member consisting of a single element.

8. The electrosurgical device of claim 1, wherein said cutting and cauterizing means comprises an electrocautery pencil, said pencil comprising an electrode tip, wherein said tip and said tubular housing are in a straight form, parallel to one another.

9. The electrosurgical device of claim 8, wherein said tip is an extension of said vortex means.

10. An electrosurgical device adapted to remove smoke from the air created by said device, said device comprising a hollow tube for evacuating the smoke, a tubular housing including vortex means extending up to an entrance end of said tubular housing for creating a vortex at said entrance end of the tubular housing, and an exit end of the tubular housing connected to one end of the hollow tube, another end of the hollow tube connected to a suction means for creating suction to remove the smoke from the air near said device, wherein said vortex means is a helical member forming at least one opening at said entrance end with an inside surface of said tubular housing through which the smoke enters said entrance of said tubular housing said device further comprising an electrocautery pencil engaged to said tubular housing, said pencil comprising an electrode tip, wherein said tip and said tubular housing, including said vortex means, are in a straight form, parallel to one another.

11. The electrosurgical device of claim 10, further comprising a valve for turning said suction means on and off.

12. The electrosurgical device of claim 10, wherein the vortex means comprises a helical member approximately one inch long.

13. The electrosurgical device of claim 10, wherein the vortex means is a helical member forming a plurality of openings at said entrance end with an inside surface of the tubular housing through which the smoke enters at the entrance end of the tubular housing.

14. The electrosurgical device of claim 10, wherein the vortex means is a helical member extending across the inside of said tubular housing.

15. The electrosurgical device of claim 10, wherein said helical member extends through the center of said tubular housing.

16. The electrosurgical device of claim 10, wherein said tip is an extension of said helical member.

17. The electrosurgical device of claim 10, wherein said helical member consists of a single element.

* * * * *